(12) United States Patent
Vandersluis et al.

(10) Patent No.: US 11,742,063 B2
(45) Date of Patent: *Aug. 29, 2023

(54) AGGREGATION AND VIEWING OF HEALTH RECORDS RECEIVED FROM MULTIPLE SOURCES

(71) Applicants: Kirstan A. Vandersluis, Colorado Springs, CO (US); IVan Fan, Colorado Springs, CO (US)

(72) Inventors: Kirstan A. Vandersluis, Colorado Springs, CO (US); IVan Fan, Colorado Springs, CO (US)

(73) Assignee: CONNETIX CORP, Colorado Springs, CO (US)

( * ) Notice: Subject to any disclaimer, the term of this patent is extended or adjusted under 35 U.S.C. 154(b) by 361 days.

This patent is subject to a terminal disclaimer.

(21) Appl. No.: 16/297,164

(22) Filed: Mar. 8, 2019

(65) Prior Publication Data
US 2019/0206531 A1 Jul. 4, 2019

Related U.S. Application Data

(63) Continuation-in-part of application No. 15/905,821, filed on Feb. 26, 2018.
(Continued)

(51) Int. Cl.
*G16H 10/60* (2018.01)
*G16H 15/00* (2018.01)
(Continued)

(52) U.S. Cl.
CPC ............ *G16H 10/60* (2018.01); *G16H 15/00* (2018.01); *G16H 30/40* (2018.01); *G16H 50/20* (2018.01);
(Continued)

(58) Field of Classification Search
CPC .......... G16H 10/00; G16H 80/00; G06F 1/00; G06F 2221/00; G06Q 10/00; G06Q 2250/00
(Continued)

(56) References Cited

U.S. PATENT DOCUMENTS

2004/0060007 A1* 3/2004 Gottlob ............... G06F 16/8358
707/E17.131
2008/0294507 A1* 11/2008 Reiner ................... G16H 15/00
705/7.41
(Continued)

FOREIGN PATENT DOCUMENTS

WO WO-2016003525 A2 * 1/2016 ........... G06F 21/606

OTHER PUBLICATIONS

Sumathi, R; Scehss: Secured Cloud Based Electronic Health Record Storage System with Re-Encryption at Cloud Service Provider; nternational Journal of Computer and Communication Engineering 2.2: 162. IACSIT Press (Year: 2013).*

*Primary Examiner* — Hiep V Nguyen
(74) *Attorney, Agent, or Firm* — Chhabra Law Firm, PC

(57) ABSTRACT

A system and method is described that automatically collects health information from multiple health data provider sources, combines it into a database, then provides a view of the information on a body map. The body map can be a drawing, photograph, or other visual model, and can be changed over time as the patient advances in age. While the image may change over time, the system continues to plot the information in the correct body location.

20 Claims, 16 Drawing Sheets

Related U.S. Application Data

(60) Provisional application No. 62/463,710, filed on Feb. 26, 2017.

(51) Int. Cl.
*G16H 50/20* (2018.01)
*G16H 50/30* (2018.01)
*G16H 50/50* (2018.01)
*G16H 30/40* (2018.01)
*G16H 80/00* (2018.01)
*G16H 30/20* (2018.01)

(52) U.S. Cl.
CPC ............. *G16H 50/30* (2018.01); *G16H 50/50* (2018.01); *G16H 30/20* (2018.01); *G16H 80/00* (2018.01)

(58) Field of Classification Search
USPC ............................................................ 705/3
See application file for complete search history.

(56) References Cited

U.S. PATENT DOCUMENTS

| | | | |
|---|---|---|---|
| 2010/0070448 A1* | 3/2010 | Omoigui | H01L 27/1463 706/55 |
| 2013/0325493 A1* | 12/2013 | Wong | G16H 50/20 705/2 |
| 2014/0067414 A1* | 3/2014 | Choi | G16H 50/50 705/2 |
| 2016/0034713 A1* | 2/2016 | Ramirez | H04L 63/0428 713/168 |
| 2016/0283667 A1* | 9/2016 | Rachapalli | G16H 10/60 |

* cited by examiner

| id | username | password | email | firstName | lastName | dateOfBirth |
|---|---|---|---|---|---|---|
| 1 | parent1 | ******** | parent1@mymail.com | John | Smith | 2/15/1988 |
| 2 | littlemike | ******** | | Michael | Smith | 6/21/2010 | figure 3

| userId | accountManager |
|---|---|
| 2 | 1 |

Figure 4

| id | name | interfaceAddress | script |
|---|---|---|---|
| 1 | Everest Family Practice | https://efp.com/portal | /conf/providers/epf.js(provider.interfaceAddress, fetchJobs.username, fetchJob.password) |
| 2 | Peak Orthopedic | https://peakorthopedic.com/portal | /conf/providers/peakortho.js(provider.interfaceAddress, fetchJob.username, fetchJobs.password) |

Figure 5

| userId | providerId | username | password |
|---|---|---|---|
| 1 | 1 | jsmith | ******** |
| 1 | 2 | johnsmith | ******** |
| 2 | 1 | michaelsmith | ******** |

Figure 6

| id | userId | providerId | codeType | code | date | problem | mapX | mapY | textX | textY |
|---|---|---|---|---|---|---|---|---|---|---|
| 1 | 1 | 1 | snomed-ct | 43878008 | 12/15/2016 | Sore throat | 250 | 125 | 400 | 125 |
| 2 | 1 | 2 | snomed-ct | 125599006 | 8/03/2012 | Broken wrist | 85 | 360 | 20 | 360 |

Figure 7

```
var destinationPath = "work/kirstan/landing/";
var casper = require('casper').create({
    verbose: true,
    logLevel: 'info',
    pageSettings: {
        loadImages: false,      // The WebPage instance used by Casper will
        loadPlugins: false,     // use these settings
        userAgent: 'Mozilla/5.0 (Macintosh; Intel Mac OS X 10_7_5) AppleWebKit/537.4 (KHTML, like Gecko) Chrome/22.0.1229.94 Safari/537.4'
    }
});
casper.options.viewportSize = {width: 1600, height: 950};
require("utils").dump(casper.cli.args);
require("utils").dump(casper.cli.options);
// Check for command line arguments and exit if not provided.
if(!(casper.cli.has("user") && casper.cli.has("pass"))){
    console.log("Please provide appropriate command line arugments! Ex. --user=test@mail.com --pass=qwerty123");
    casper.exit();
}
var username = String(casper.cli.get("user"));
var password = String(casper.cli.get("pass"));
var url = casper.cli.get("url");
if (!url)
    url = "https://portal.mvmg.com/portal/Login.aspx";

//1. Open up MVMG Patient Portal Login Screen and fillout login information.
casper.start(url).thenEvaluate(function(username,password)
{
document.getElementById("txtUsername").value=username;
document.getElementById("txtPassword").value=password;
},username,password);

//2. Setfocus
casper.then(function(){
    // Set the focus to allow clicking the login button.
    this.mouse.click(200, 300);
});

//3. Login!
casper.then(function(){
    this.evaluate(function(){
        document.getElementById("btnLogin").click();
    });
});

//4. Go to chart-summary page
casper.thenOpen("https://portal.mvmg.com/portal/chart-summary/default.aspx",
function(){
});

//5. Render COMPLETE CHART SUMMARY.
casper.then(function() {
    this.evaluate(function(){ document.getElementById("mc_Content_GenericTabs_GenericTabs_lbtnCompleteMedicalRecord").click();
    });
});

// 6. Download Complete Chart Summary
casper.then(function() {
    this.evaluate(function(){ document.getElementById("btnDownload").click();
    });
});
casper.on('resource.received', function (resource){
    "use strict";
    if((resource.url.indexOf("/Chart-Summary.zip") !== -1)){
        var url, file;
        url = resource.url;
        file = "Chart-Summary.zip";
        try {
            var fs = require('fs');
            casper.download(resource.url, destinationPath + file);
        }
        catch(e) {
            this.echo(e);
        }
    }
});
casper.run();
```

Figure 11A

```
<Lookup>
<!-- terms with corresponding body location -->
<Map id="bodyLocation" default="0:286,70" desc="Body location term and nominal location">
    <Item key="RHINITIS">0:286,115</Item>
    <Item key="Nose">0:286,112</Item>
    <Item key="VIRAL SYNDROME">0:287,176</Item>
    <Item key="Throat">0:287,180</Item>
    <Item key="TINNITUS">0:253,139</Item>
    <Item key="Left Ear">0:253,142</Item>
    <Item key="Right Ear">0:324,142</Item>
    <Item key="Ear">0:324,142</Item>
    <Item key="Neck">0:273,168</Item>
    <Item key="Face">0:303,122</Item>
    <Item key="HEADACHE">0:297,90</Item>
    <Item key="Insomnia">0:286,70</Item>
    <Item key="shoulder">0:365,213</Item>
    <Item key="left shoulder">0:365,213</Item>
    <Item key="right shoulder">0:213,213</Item>
    <Item key="wrist">0:286,70</Item>
</Map>
</Lookup>
```

Figure 12

```
1300 ┌─────────────────────────────────────────────────────────┐
     │ Connect, by a computer system, to at least one healthcare data provider │
     │                         1302                            │
     └─────────────────────────────────────────────────────────┘
                               │
                               ▼
```

- 1300
- Connect, by a computer system, to at least one healthcare data provider
  1302
- Provide information related to a user to the at least one healthcare data provider, the information including authorization credentials related to the user
  1304
- Retrieve a healthcare dataset related to the user, wherein the healthcare dataset includes a set of medical information related to the user
  1306
- Determine a corresponding location on a canonical body map related to each medical information in the set of medical information
  1308
- Associate the corresponding location and each respective medical information
  1310
- Provide a view of the canonical human body map to the user, on a graphical user interface, wherein the canonical body map provides markings at each location related to each respective medical information based on the associating
  1312
- Display medical information related to a marking on the canonical body map through the graphical user interface.
  1314

FIG. 13

AGGREGATION AND VIEWING OF HEALTH RECORDS RECEIVED FROM MULTIPLE SOURCES

FIELD OF INVENTION

The present invention relates to aggregating, viewing, and distributing patient health records from multiple sources. Specifically, the present invention relates to aggregating health records about a patient from various sources and then presenting them in an organized fashion on a graphical user interface.

CROSS-REFERENCE TO RELATED APPLICATIONS

This application is a continuation-in-part of, and claims the benefit of U.S. patent application Ser. No. 15/905,821, filed Feb. 26, 2018, which further claims priority from U.S. Provisional Application Ser. No. 62/463,710, filed Feb. 26, 2017. Both identified applications are hereby incorporated by reference in their entirety.

BACKGROUND OF THE INVENTION

Providers maintain records of patients in computer systems (electronic medical records-EMR systems) or on paper. The typical person in the US has 5 to 10 healthcare providers. A person will then have health records spread across 5-10 different systems. This severely limits the patient's ability to have a complete view and understanding of their health condition. A patient with full access to their health information has a higher likelihood of successful health outcomes.

Lack of control over health information creates inertia in healthcare delivery from the patient's and provider's perspective. Patients feel tied into current providers, making it seem infeasible to find the best valued/treatment provider at any given time. When changing providers, the new provider ideally needs to access the patient's records before providing adequate treatment. The result is that healthcare capacity is not efficiently used to the detriment of both patients and providers.

Thus, what is needed is systems and methods for patients to take control of and manage their health records to overcome the above mentioned deficiencies.

SUMMARY

The present invention comprises a system and method to configure a system to automatically collect health records from multiple providers, collect the data, then normalize the data into a common format for presentation, analysis, predictive diagnosis, and other processes, then store the data for long term (life long) use, avoiding the reliance on individual providers to store data (as these change from time to time, causing permanent loss of information).

The combined set of records are projected onto several views to aid in rapid viewing and understanding of a user's health. The views are intended for both patient and provider understanding of health history and current conditions to increase efficiency in health care delivery. Views allow filtering of data to enable the user to see information of interest. Dimensions of filtering include medical areas (orthopedics, dermatology, internal medicine, etc.), status of the condition (new, ongoing/chronic, recovered/corrected, etc.), time range, and others.

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes a system configured to connect to at least one healthcare data provider; submit information related to a user to the at least one healthcare data provider, the information including identification and/or authorization credentials related to the user; retrieve a healthcare dataset related to the user, where the healthcare dataset includes a set of medical information related to the user; determine a corresponding location on a canonical body map related to each medical information in the set of medical information; associate the corresponding location and each respective medical information; and provide a view of the canonical body map to the user, on a graphical user interface, where the canonical body map provides markings at each location related to each respective medical information based on the associating. The system can also be configured to displaying medical information related to a marking user on the canonical body map through the graphical user interface. Other embodiments of this aspect include corresponding computer systems, apparatus, and computer programs recorded on one or more computer storage devices, each configured to perform the actions of the methods.

Implementations may include one or more of the following features. In one embodiment, the canonical body map can be replaced with an alternate rendition, such as a photographic image of the user's body. In yet another embodiment, submitted information related of the user to the at least one healthcare data provider includes transmitting an attribute associated with a script, where the script is configured to connect to a database associated with the healthcare data provider to retrieve the healthcare dataset related to the user. In one embodiment, a list of locations is preconfigured to correspond to each location on the canonical body map. In one embodiment, retrieving the healthcare dataset includes navigating through at least one web page configured in a website of the at least one healthcare data provider. In one embodiment, retrieving the healthcare dataset includes invoking an appropriate link or command to download a health data set from the website. In one embodiment, the credentials are preconfigured by a user and stored in the storage media for each health data provider. In another embodiment, a trust relationship with the health data provider is pre-established, and a secure connection is used whereby user identity information is passed to the health data provider, and the health data provider returns the healthcare dataset related to the user. Yet, in one embodiment, the medical information includes at least one of a health condition, procedure, or laboratory results related to the user. Implementations of the described techniques may include hardware, a method or process, or computer software on a computer-accessible medium.

BRIEF DESCRIPTION OF THE DRAWINGS

For a more complete understanding of the present invention and its features and advantages, reference is now made to the following description, taken in conjunction with the accompanying drawings, in which:

FIG. 3 illustrates a database table named "user" to store information for the one or more instances of a user of the system, according to one aspect of the invention.

FIG. 4 illustrates a database table named "'accountManager" to store a relationship between users such that one user is given permission to view health information of another as in the case of a care giver providing care to a child or elderly parent, according to one aspect of the invention.

FIG. 5 illustrates a database table named "provider" to store information about health record provider systems that contribute health records to a user's overall health information, according to one aspect of the invention.

FIG. 6 illustrates a database table named "fetchJob" to store information about which health data provider system to connect to, along with credential information (user name and password, for example), according to one aspect of the invention.

FIG. 7 illustrates a database table named "record" to store information about a health problem and its location on a visual body map, according to one aspect of the invention.

FIG. 11A illustrates computer instructions to retrieve health information from a health data provider, according to one aspect of the invention.

FIG. 12 illustrates a reference table where key words relating to the human body are translated to coordinates on a canonical body map, according to one aspect of the invention.

FIG. 13 illustrates the operations to perform the tasks to aggregate health records about a patient from various sources and then presenting them, according to one aspect of the invention.

DETAILED DESCRIPTION

Various embodiments and aspects of the inventions will be described with reference to details discussed below, and the accompanying drawings will illustrate the various embodiments. The following description and drawings are illustrative of the invention and are not to be construed as limiting the invention. Numerous specific details are described to provide a thorough understanding of various embodiments of the present invention. However, in certain instances, well-known or conventional details are not described in order to provide a concise discussion of embodiments of the present inventions.

Reference in the specification to "one embodiment" or "an embodiment" or "another embodiment" means that a particular feature, structure, or characteristic described in conjunction with the embodiment can be included in at least one embodiment of the invention. The appearances of the phrase "in one embodiment" in various places in the specification do not necessarily all refer to the same embodiment. The processes depicted in the figures that follow are performed by processing logic that comprises hardware (e.g., circuitry, dedicated logic, etc.), software, or a combination of both. Although the processes are described below in terms of some sequential operations, it should be appreciated that some of the operations described can be performed in a different order. Moreover, some operations can be performed in parallel rather than sequentially.

A table as referred to herein, means a data structure that can store a logical table. Therefore, a table, as referred to herein can be one database table, a series of tables, text files, binary files, or any other structure that can store and associate information across one or more non-transitory computer readable medium(s). Accordingly, the following detailed description should not be limited to the disclosed embodiments and examples. Instead, the proper scope is defined by the appended claims.

Figure 1:
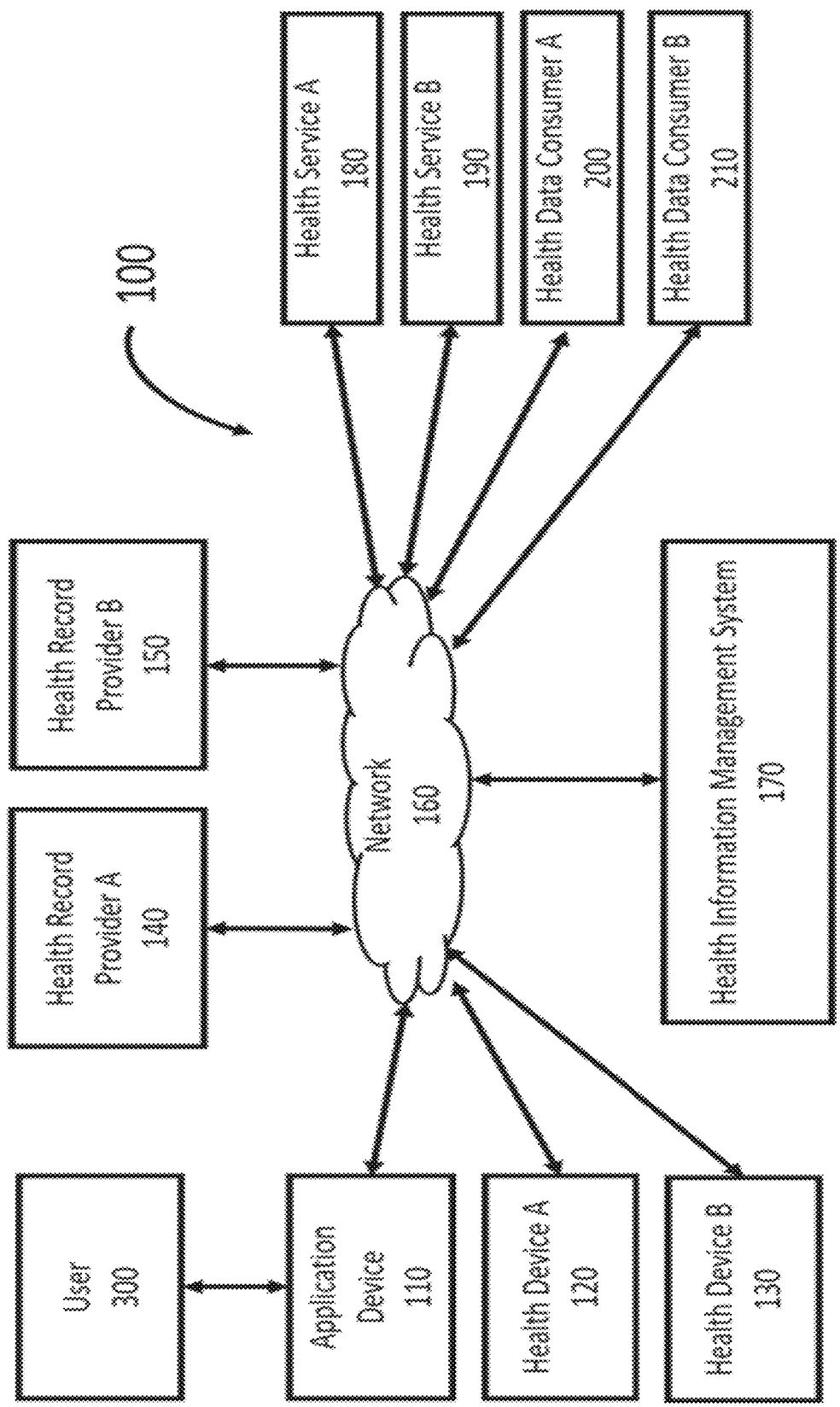
FIG. 1 illustrates an exemplary system environment wherein the system for integrating and distributing health records operates, according to one aspect of the invention.

The present disclosure enables accessing health records from many sources in order to provide benefits to the patient, family, providers, and caregivers. FIG. 1 shows an environment of systems 100, connected by a network 160, whereby systems can communicate with one another in a secure manner to allow health records to be accessed. The environment may comprise a network 160, an application device 110 which is a device that can interact with a human user 300, a system which manages electronic health records with a means to distribute information, for example health record provider A 140 and health record provider B 150, a health device A 120, health device B 130, a health information management system 170, a health service A 180, a health service B 190, a health data consumer A 200, and a health data consumer B 210.

In an exemplary environment of systems 100, in which embodiments consistent with the present disclosure may be practiced and implemented, the systems are able to communicate securely with one another, in a manner reflecting the security policies of each system. For example, the system 170 may be configured to receive data over an electronic network 160 (e.g., the Internet), from health record provider A 140, analyze the data, incorporate the data into a database, then transmit a merged or combined data set from the database to another system, such as application device 110, which may in turn display the information to a user 300.

The following paragraphs describe the characteristics of example systems in the environment of systems 100 connected by a network 160 as shown in FIG. 1.

Application device 110 is a device such as a mobile phone or internet browser, which is capable of showing the health information transferred to it from the health information management system 170.

Health device A 120 and health device B 130 are health devices that can perform a health monitoring function such as measuring blood pressure, heart rate, or weight, and transmit that data over the network 160 to the health information management system 170.

Health record provider A 140 and health record provider B 150 are examples of systems that store health records associated with patients and make those records, or portions thereof, available to patients or their representatives through various technical means. An example of this type of system is an electronic health record (EHR) system in use by a health provider where a user 300 receives care, and providers enter information about the user 300. An EHR may make the information available via a patient portal, where a user 300 can log in via an application device 110 and network 160, navigate to the appropriate page, and download the records in a predefined format. An EHR may alternatively make the data available through an application programming interface (API) using predefined interface mechanisms and formats.

A health service A 180 and health service B 190 are examples of systems that provide a service on behalf of the user 300 by examining the data transferred by the health information management system 170 on behalf of the user 300, performing some function such as a medical diagnosis, then returning the result to the health information management system 170 for later use of the user 300.

A health data consumer A 200 and health data consumer B 210 are examples of systems representing organizations that are interested in receiving and processing health data for their own purposes, for example a medical research organization or a population health organization. The health information management system 170 is capable of sending health information to these systems upon authorization by the user 300.

The health information management system 170 is a system that manages health information on behalf of a user 300. It collects information from other systems such as application device 110, health record provider A 140, health record provider B 150, health device A 120, health device B 130, health service A 180, and health service B 190, where the data is manipulated and stored for later use.

A user 300 of application device 110 may be a patient, or may be a caregiver such as a parent in the context of caring for her child. A user 300 could be both a patient and caregiver, in which case it is beneficial for health information to be accessible for both the patient and individuals for which the user provides care. The present disclosure allows the user to view and manage her own health information accessed from one or more sources, and to view and manage health information for one or more patients for which she is given authorization. The user can view the health information, and control the information which flows to presentation to patients, family, and caregivers, and how the newly combined data is useful for advanced purposes benefiting the patient and the broader healthcare industry.

All data is managed in a highly secure manner compliant with security standards such as NIST 800-53 and HIPAA compliant technology guidelines. Data is encrypted both at rest in the health information management system 170 and while in transit across the network 160.

Each system within the environment 100 is capable of managing data on behalf of a particular user 300, in a manner that ensures that data is appropriately associated with a specific user, so that data associated with a specific user is not unintentionally mixed together with data associated with other users.

Figure 2:
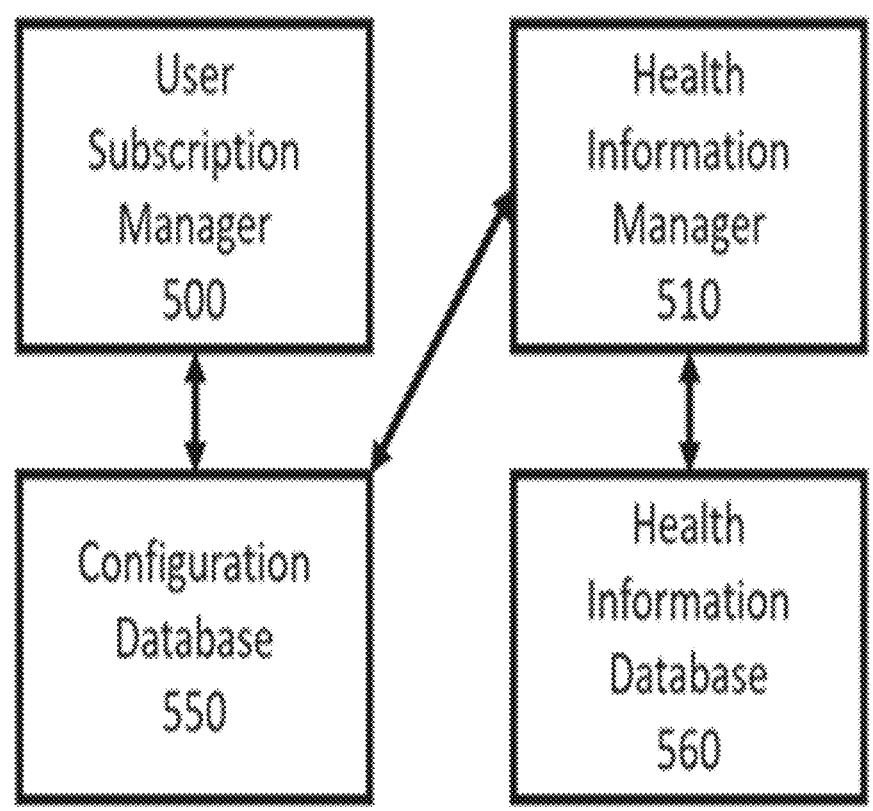
FIG. 2 illustrates an exemplary health information management system, according to one aspect of the invention.

The present disclosure describes how a user 300 can subscribe to a service and provide instructions for collecting health information from multiple sources, and display the information on a single device. FIG. 2 illustrates an exemplary set of components which provide the capability for health information management system 170. A user subscription manager 500 enables a user 300 to subscribe to the services for the health information management system 170. In one embodiment of the disclosure, when a user 300 wishes to subscribe, the user subscription manager 500 collects a user name, password, email address, name, and other attributes as shown in FIG. 3, the "user" table. This information is stored and maintained in the configuration database 550. In this example, two users are shown, named John Smith and Michael Smith. One skilled in the art would collect this information from the user with a suitable interface, ensure the password follows adequate security guidelines, and the email address is valid. If one of the users is a child of another user, as could be the case in this example (note the same last name and large difference in dates of birth), the primary care giver would set up the user account for the dependent. Note that the password field is shown as asterisks. A real password would be stored as a hash so that the password is not known by anybody except the user that created the account. An attempt to recover the password by a user would follow the standard conventions that a new password would need to be created. In this disclosure, password fields are always shown as asterisks. In the user table in FIG. 3, the "id" field is a unique identifier for a record. Username is a unique name identifying a user, email is the email address for a user. Other attributes include the users first name "firstName", last or surname "lastName", and date of birth "dateOfBirth". The id field is a unique identifier for the user which will be used to relate other information in other tables, including health records, health data providers, and other information. The username and password field are examples of credentials for a user 300 to log into the application device 110, and will be verified by the health information management system 170, after which the user 300 will be shown information from the health information management system 170.

To support a caregiver relationship, one user may manage the account of another. In that case, a relationship must be established and tracked to enforce this relationship. FIG. 4, table "accountManager" is configured to show a relationship that for the user with userId 2, which corresponds to the user record for Michael Smith in FIG. 3 user table, the user with userId 1 is an account manager. As user with ID 1 is John Smith in FIG. 3 user table, John Smith will be enabled to view all the information with the account for Michael Smith. This table is stored and maintained in the configuration database 550.

In a preferred embodiment of the invention, a configuration database 550 stores information about one or more health record providers such as health record provider A 140 and health record providers B 150, using a database table format as shown in FIG. 5, "provider" table. This table is managed by configuration database 550. Each record in this table identifies a health data provider which the system is capable of connecting to, and retrieving health information. The "id" attribute is a unique identifier for the record, the "name" attribute is a readable name representing the data source, for example the name of the practice with a patient portal that the system will connect to, the interface Address attribute is an address, often a universal resource locator (URL), and the "script" attribute is the name of an executable script that is designed to connect to the data provider system, navigate as needed, and read or download related health information. In a preferred embodiment of the invention, the script field also enumerates the parameters needed by the script, such as the interfaceAddress, and credentials (username and password for example) for the user whose health information will be retrieved. For example, executing the script "/conf/providers/epf.js" and providing parameters "efp.com/portal", "jsmith", and "******" its corresponding password will result in these data values being passed at runtime to the script, where the script will log into a portal at that interface address using the username "j smith" and supplied password, in order to read or download current health information to incorporate into the system. The provider table is stored and maintained in the configuration database 550. This database and table is configured to be accessible from Health Information Manager 510 and User Subscriber Manager 500**.

In a preferred embodiment of the invention, FIG. 6 shows a database table, "fetchJob", which lists the health data providers to access, and the credentials (user name and password for example) needed to access each health data provider. In the example, the user represented by userId 1, has two records configured, each to access two different health data providers, including the health data provider with identifiers 1 and 2, which reference corresponding records in the "provider" table shown in FIG. 5. Linking the providerId to the corresponding ID in the provider table, the example indicates that the Everest Family Practice data provider will be accessed with username "jsmith" (first data record, FIG. 6), the Peak Orthopedic data provider will be accessed with username "johnsmith" (second data record, FIG. 6), and the Everest Family Practice data provider will be accessed with username "michaelsmith" (third data record, FIG. 6). The first two health data sets will be associated with user with identifier 1 "John Smith", and the third with user with identifier 2 "Michael Smith". The "fetchJob" table is stored and maintained in the configuration database 550.

In one embodiment of the invention, FIG. 7 shows a database table, "record", which is a highly simplified definition of a health record, describing a condition, problem, procedure, or other aspect which is considered "health information". In the example, two records are shown, both associated with the user with identifier 1 "John Smith" as indicated by the userId field. Each record contains information about a health problem, the health data provider from which it came (indicated by providerId field), a code representing the problem "code", and the code system from which the code is defined ("codeType"), a description of the health problem or information item ("problem"), and location information which shows where on a 2 dimensional canonical body map the problem occurs (mapX, mapY), and a location on the body map view where a textual description is placed (textX, textY). The codeType, code, date, and problem attributes are examples of data retrieved from a health data provider A 140 or health data provider B 150. The map location and text location information is calculated or derived from the retrieved data. The location information is relative to a coordinate system defined in terms of a canonical body map as will be described in a later section.

The "record" table is stored and maintained in the health information database 560.

Figure 8:
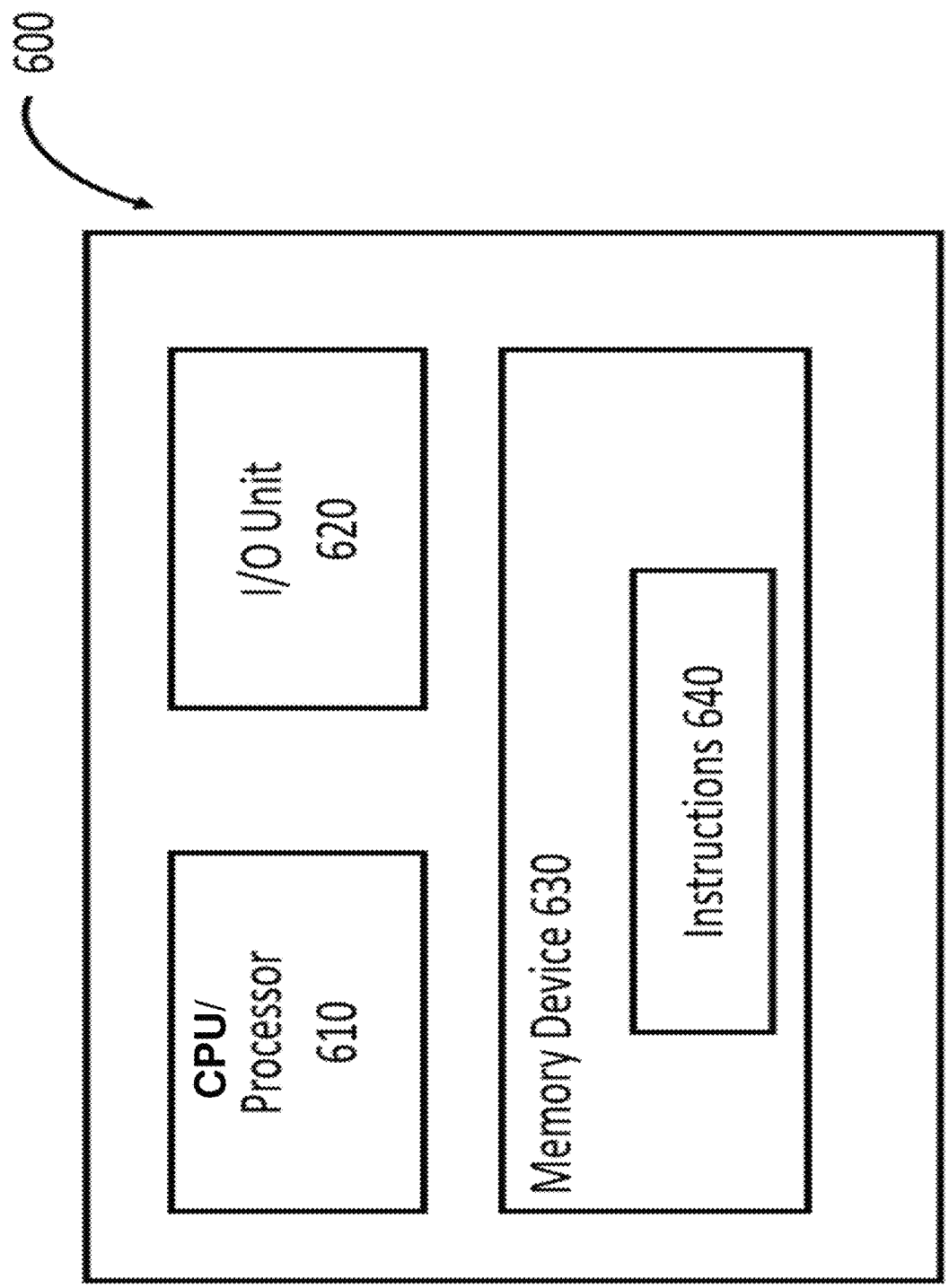
FIG. 8 illustrates a computer system, an instance of which is used for each system as described in the following sections, according to one aspect of the invention.

In a preferred embodiment of the invention, a health information manager 510 is a computer with an architecture as shown in FIG. 8. Such a system may comprise one or more storage mediums or memory devices, storing computer readable instructions for retrieving health information from one or more health data providers A 140 or health data provider B 150.

The various components of the system 600, illustrated in FIG. 8, may include an assembly of hardware, software, and/or firmware, including a memory device 630, a central processing unit ("CPU") 610, and/or a user interface using the input/output unit 620. Memory 630 may include any type of RAM or ROM embodied in a physical storage medium, such as magnetic storage including floppy disk, hard disk, or magnetic tape; semiconductor storage such as solid state disk (SSD) or flash memory; optical disc storage; or magneto-optical disc storage. A CPU may include one or more processors, such as processor 610, for processing data according to a set of programmable instructions 640 or software stored in the memory 630. The functions of each processor 610 may be provided by a single dedicated processor 610 or by a plurality of processors. Moreover, processors may include, without limitation, digital signal processor (DSP) hardware, or any other hardware capable of executing software. An optional user interface may include any type or combination of input/output devices 620, such as a display monitor, keyboard, touch screen, and/or mouse. Such a computer system 600 is an embodiment of the invention that supports the processing needs of application device 110 and health information management system 170, each having their respective instructions 640 to specify the processing as described in later sections.

In a preferred embodiment of the current invention, the health information manager 510 periodically gathers health information as configured in the database tables previously mentioned. On a periodic interval (e.g. once per day), the health information manager 510 examines each user in the user table in the configuration database 550.

For a given user, the health information manager 510 examines all entries in the fetchJob table. In one embodiment, health care information manager can be configured to examine a provider table corresponding to the fetchJob record, which describes how to gather health information for this user from the indicated health data provider. Health information manager 510 can also be configured to establish a connection to the resource on behalf of the user (e.g. call the designated script which will automatically log into the portal using the stored credentials) and/or follow the defined navigation path, actuating links, buttons and other resources as required and as specified in the designated script, to ultimately retrieve information from the provider (health record provider A, health record provider B). In one embodiment, health information manager 510 can check if the information retrieved is already contained in the Health Information Database 560, and if it is not new, continue to the next item without storing any information. Health information manager 510 can also get the health information from the information received. In one embodiment, if codes are provided (ICD9, ICD10, SNOMED-CT, etc), then those can be converted into readable text using common lookup techniques. In one embodiment, the conversion of codes to readable text occurs at run-time. In another embodiment, the conversion of codes into readable text occurs at the time of retrieval of the information. Health information manager 510, in one embodiment, can create a record in the "record" table to store the retrieved health information and/or can also create a "natural key" for the information, based on predefined attributes in the item.

In one embodiment, the natural key is stored as an additional column in the record table. A health record natural key can include a SNOMED-CT code, code system, date, provider, etc. The natural key is selected to enable de-duplication of this item from the same or other resources. The user may later choose to relate items from different resources to designate them as the same incident, condition, etc. The natural key is used for this purpose. The deduplication method may be extended to take advantage of the hierarchy of terms in the code system used, so that specific terms are known to be related to ancestors in the term hierarchy, and may therefore refer to the same incident, condition, etc. In one embodiment, the user may also add notes related to this item to provide his/her personal information related to this incident/condition. The user may designate through manual indication that the record is related to an existing record, and that the two should be shown as a single incident, condition, etc.

Health information manager 510 can also be configured to look up the location on the canonical body map for the described item. In one embodiment, each term in the item description is used to search the body map keyword reference data for a body map location. The configuration database can include a table with data similar to that represented in FIG. 12 (which is a sampling of data), whereby a word is searched to find the location on the canonical body map. Each word in the problem description is searched until a match is found. In another embodiment, if an ICD-9 or ICD-10 code is available, it is mapped to a SNOMED-CT code using common lookup table technologies, then the SNOMED-CT code is examined to find the corresponding "finding site" attribute, which is a body structure term in the SNOMED-CT data set.

In one embodiment, a lookup table is provided which maps every SNOMED-CT body structure term to a location on the canonical body map. This information is stored in a format similar to FIG. 12 wherein a key indicates a SNOMED-CT body structure and the corresponding values identify a body map and coordinate location on that map. The canonical body location is stored along with the record. Thus, a condition is first translated to a body structure term, then the body structure term is translated to a coordinate location on the canonical body map. The user is later allowed to move this to a different body map point at his/her discretion, useful when the automated means are not accurate or the user otherwise chooses a different location, in which case the new location replaces the old location in the record table.

Health information manager 510 can also, in one embodiment, create a location for a visual text summary of the item, to be shown along with the body map. The summary text is shown in a box with color or other visual indication to designate whether the item represents a new condition, ongoing condition, or resolved condition. The location of the text is calculated to be close to the body map location, and not overlapping with the body map or other text boxes to the extent possible. A line with similar visual indications is drawn from the text box to the body map location. In order to handle large amounts of information, filters are provided to allow the user to select categories of information (e.g. dermatology, orthopedic, internal, etc). Also, a time filter can be applied to show only a time window of information, for example, conditions with onset dates between ages 45 and 55.

Health information manager 510 can also be configured to store information to health information database 560, associated with the current user, the item with its natural key, both in original item form, and in a derived form where codes and other derived information is present (e.g. body map information).

In one embodiment, application device 110 lets the user view the health information for themselves and for their family members, following permissions granted in the accountManager table FIG. 4. When a user views their information in an application device 110 (web browser or mobile device application), the following processing is performed:

Application device 110 can present the health information on a body map. As described earlier, each information item that is relevant to the body map, is shown in a text box with particular color or other visual indication to designate whether the item represents a new condition, ongoing condition, or corrected condition. The location of the text is calculated to be close to the body map location, and not overlapping with the body map or other text boxes to the extent possible. A line with similar visual indications is drawn from the text box to the body map location. In order to handle large numbers of information items, filters are provided to allow the user to select categories of information (e.g. dermatology, orthopedic, internal, etc). Also, a time filter can be applied to show only a time window of information. A user can scroll through their medical history for their lifetime or the lifetime a patient whose information to which they have been given access.

The user can also specify the items that may be viewed by other users and specify which items may be shared, outside the system (as when records are sent to a provider before an appointment, or when records are sent to a diagnostic system). In one embodiment, the user can create and edit new information records, add notes to existing records, or allow viewing of the items in reverse chronological order via application device 110.

The health information manager 510 provides the ability to render the information from health data providers onto various renditions of a body map. This enables a user to view health information on a realistic, photographic picture, a wire-frame, or other visual model. This capability aids the patient and caregivers in understanding of conditions, as the view more concretely corresponds to the real world subject. The health information manager 510 relates conditions to body locations when appropriate. For example, a mole located 2 centimeters directly below the center of the left eye can be plotted on a body map at a point equivalent to 2 cm below the left eye center, and an appropriate annotation in a text box can be made indicating, for example, "mole removed by nitrogen freezing". This aids the patient and caregivers in recall and understanding of the condition and treatment, especially over time when memory tends to fade.

Figure 9:
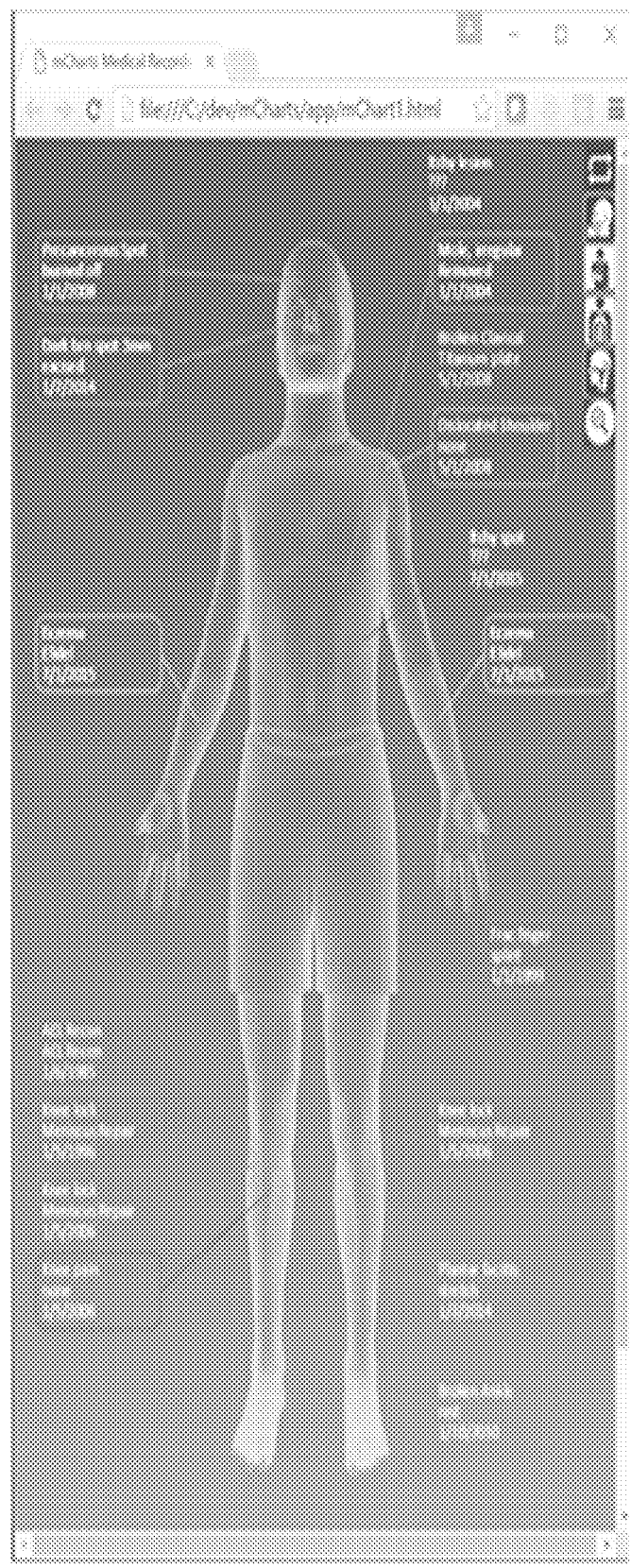
FIG. 9 is a picture of a computer screen rendered, according to one aspect of the invention.

Health information manager 510, in one embodiment, can define a canonical body map as shown in FIG. 9. This is a graphic image that is stored in the configuration database and made available to the health information management system 170 and displayed on the application device 110.

In one embodiment, mapping of conditions occurs on the canonical body map. When a textual account of a condition is stored, or a SNOMED-CT or other code is encountered representing a condition, a process is used to translate the affected body location to a point on the canonical body map. In addition, the patient or caregiver may specify explicitly the affected point on the canonical body map by pointing and clicking using a pointing device (e.g. mouse or touch-sensitive display). Further, in one embodiment, custom body shapes can be supported using a photographic morphing method. As an example, an algorithm to translate to custom body shapes from the canonical body map comprises (1) identifying key reference 3-D points on the canonical body map (x,y,z). For example, this can be implemented by defining reference points for nose, each eye center, left, right, top, and bottom edges of mouth, tip of chin, belly button, each shoulder, each elbow, each wrist, each finger tip, low point of groin, outer edge of each hip, knee, ankle, each toe tip, etc. The precision is variable depending on the desired precision and accuracy of the translation, with more reference points producing better conversion precision at the expense of more work and processing cost.

(2) identify corresponding reference points on the custom body shape (a,b,c). Maintain a correspondence between each reference point on the canonical body map and that of the custom body shape. For example, the tip of the nose may be at location (280,110,30) on the canonical body map. On the custom body map, we identify the tip of the nose using manual or automated means (image processing which can detect a specific body point). Assume this point is (1325, 1050, 330). In one embodiment, an association table that relates the point (280,110,30) to point (1325,1050,330) is maintained.

(3) for each point to be plotted onto the custom body shape (for example, a mole under the left eye as described above), start with the point on the canonical body map (x,y,z). Then translate that point onto the custom body shape (a,b,c). For example, suppose the point that needs to be plotted is exactly on a reference point in the canonical body map. Then, we simply look up the corresponding point in the custom body map and can plot on that point.

In one embodiment, points on the canonical body map that are close to a reference point should be placed close to the corresponding reference point in the custom body shape. A vector that represents the distance and direction from the reference point on the canonical body map is created. The vector is scaled as appropriate into a corresponding distance and direction from the reference point in the custom body shape. Scaling is based on the relative size between the canonical body map and the custom body shape. The plot point on the custom body shape is calculated as the corresponding reference point plus the scaled vector. In one embodiment, for points in general (that may or may not be close to a reference point), the closest reference point is found before the algorithm is applied. In another embodiment, since body shapes are irregular, a more accurate placement can be achieved by selecting several of the closest reference points, applying the above algorithm to find multiple candidate points on the custom body map, then calculating the average of these points. In one embodiment, any number of custom shapes can be defined supporting the broad spectrum of body shapes found in the general population. Further, in an embodiment, the algorithm to find the point on the custom body shape is intended as an initial approximate location. The user or caregiver will be allowed to later adjust the location to a more precise location visually using a pointing device or touch-sensitive display. Furthermore, absolute accuracy is generally not needed to communicate a condition to patient or caregiver.

While the process description above references 3-dimensional points, it should be appreciated that one skilled in the art will understand that 2-dimensional points can be processed in a similar manner.

In yet another embodiment, the 3-D model can be expanded to incorporate other dimensions, such as age. Using age as an additional dimension, the body shape can be shown in sequence through time, thus showing the growth of child, or the change in body shape, such as while dieting and losing significant weight. Thus, a condition as a child, such as broken leg when 6 years old, is properly adjusted and plotted correctly on an adult image many years later, as the canonical body map location for the broken leg is properly translated to the correct location based on the adult-sized image. In one embodiment, the processing is restricted to 2 dimensions instead of the 3 dimensions as described herein, if a flat surface map of the body is desired. Yet, in another embodiment, an additional dimension that selects the body map view (for example: front, left side, back, right side) can be used if flat views are desired. In this scenario, a location is constructed as (x,y,v), where 'v' is a flat view identifier, for example enumerating one of front, left side, back, right side views.

In one embodiment, custom shapes can also be created, and mapped to the canonical body map. These custom shapes may include lifelike body shapes, three dimensional (3D) drawing of a person, 3D rendering of a person, whether drawn or derived through automated or semi-automated means, a photograph of a person, a sequence of photographs of a person, 3D print of the person, or a combination thereof.

For example, to simulate 3D visualization, a photograph of the individual from multiple periodic angles can be provided. Thereafter, any key reference photographs onto which the reference points will be plotted can be identified (for example, on the front image and back image). Then, the application device 110 can show the front or back views with mapped conditions (after plotting condition locations and translating the points onto the photographic image as described above), and can show the photographs in sequence, which then appears to animate the rotation of the rendition, providing a visualization that appears to be three dimensional.

In one embodiment, to increase the precision of the body map locations that are desired to be plotted, a number of canonical body maps can be defined—one for each general body shape of various people across the spectrum of age, gender, weight, height, builds, length of arms, length of legs, size and shape of head, etc. There after, reference locations for each of these can be generated (or derived using the method described above, in one embodiment). Then an end user can select a body type that is similar to the user, to increase the precision of mapping the body location for a particular condition.

Following this process of mapping conditions to a canonical body map, conditions contain references to locations on this canonical bod map. Using the method described, the canonical body map location can be translated to alternate renditions of the user, such as a photograph.

Figure 10:
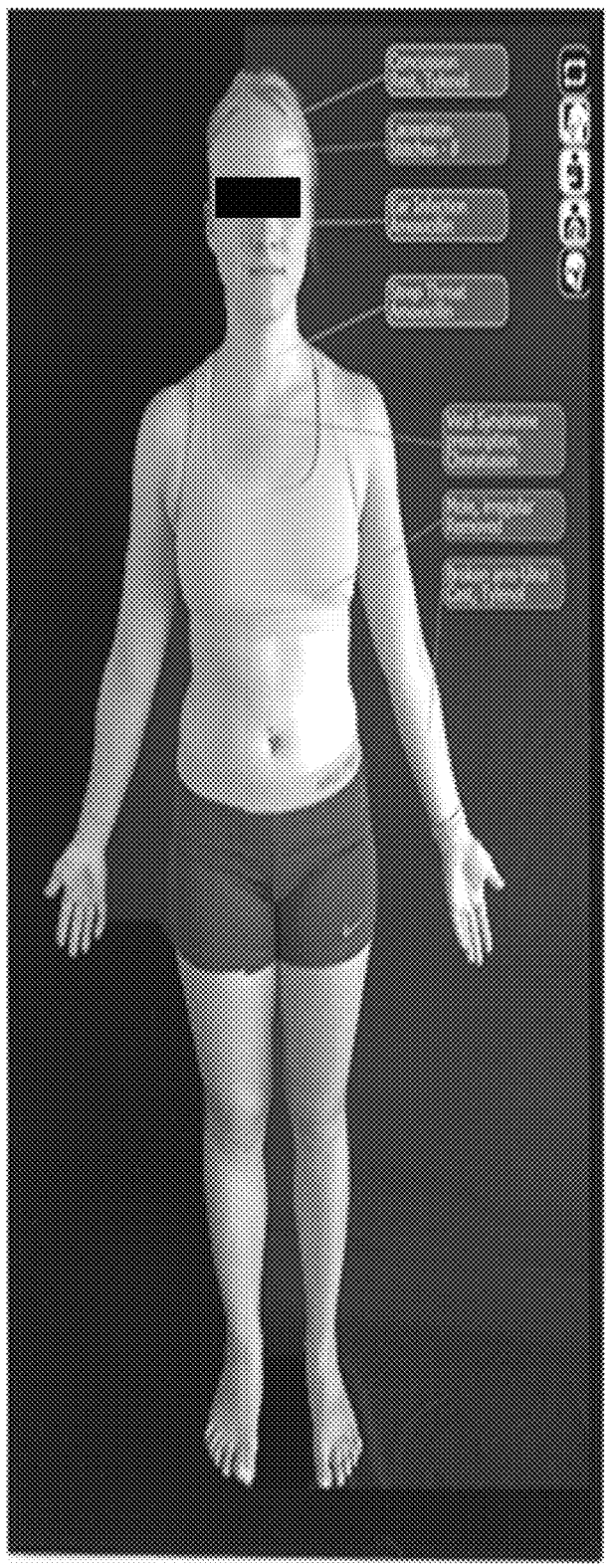
FIG. 10 is a second picture of a computer screen rendered by an embodiment of the current invention, showing a realistic photograph of a user with superimposed health information, according to one aspect of the invention.

FIG. 10 shows a photograph with conditions that have been plotted first on the canonical body map, then transformed to the proper locations in the image as described above. In a preferred embodiment of the invention, a user can create reference points for a photograph, and the conditions will be appropriately plotted on the photograph. In another embodiment, the condition can be displayed on an image representing the the user as a child. As the user ages, the image can be updated to reflect growth into later stages of life, such as adolescence or adulthood. With each photograph appropriately configured with reference points, the same condition will be appropriately rendered on each photograph n the sequence, regardless of the shape or size of the image. In another embodiment of the preferred invention, a sequence of images of a user over time can be shown as an animated sequence, whereby the image is shown to grow frame by frame, and the conditions over time continue to be shown and accurately positioned, regardless of the size or shape of the image.

The health information manager 510 gathers information from various health data providers. FIG. 11A is one exemplary script which provides executable instructions retrieving data from a health data provider. In this embodiment, the script runs in the environment CasperJS, as illustrated.

Figure 11B:
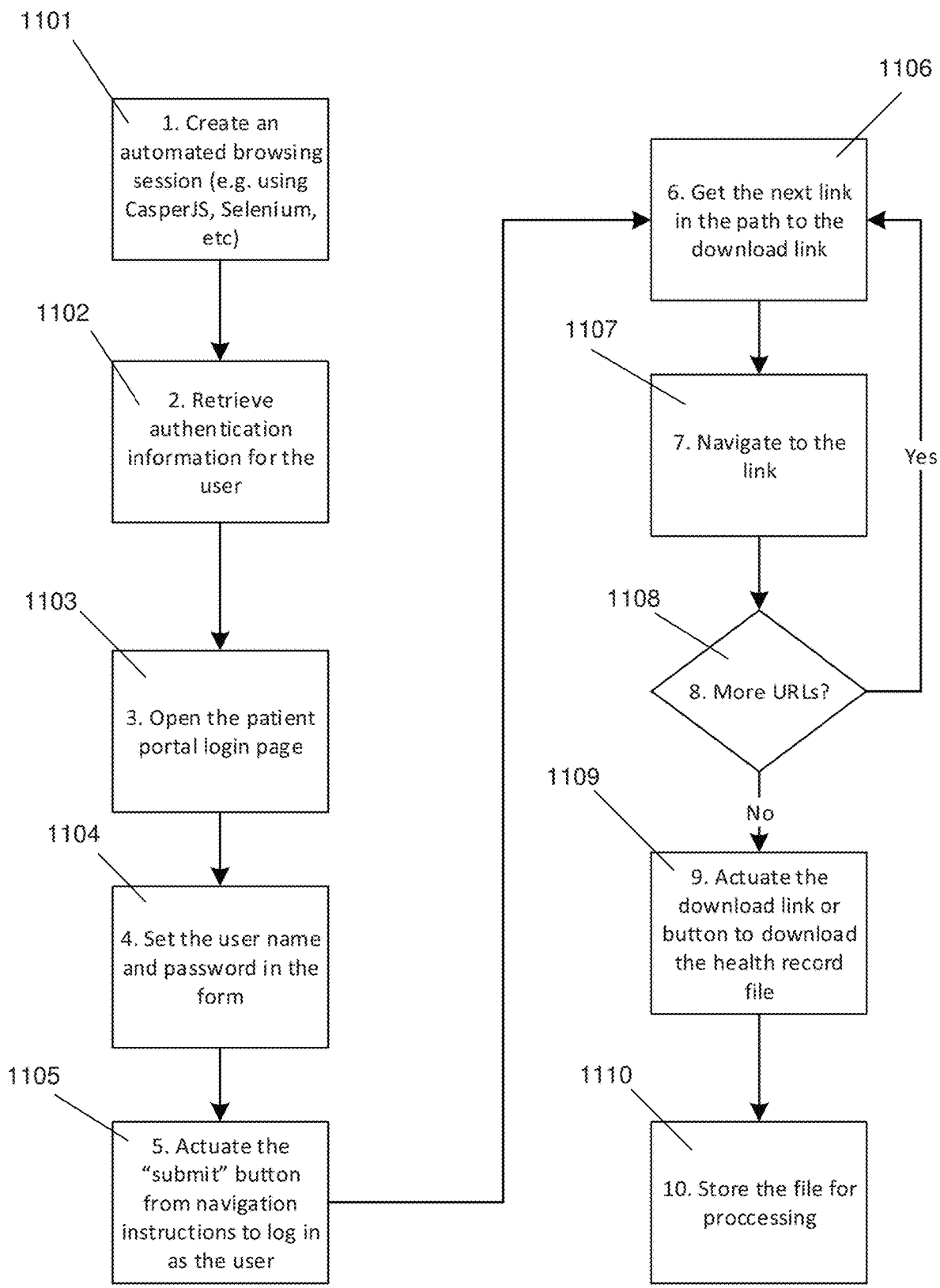
FIG. 11B is a flowchart based on the code illustrated in FIG. 11A, according to one aspect of the invention.

FIG. 11B is a flowchart based on the code illustrated in FIG. 11A.

At 1101, an automated browsing session is created. This is illustrated by the following code described in FIG. 11A:

```
const url = "portal.mvmg.com/portal/Login.aspx";
var destinationPath = "work/kirstan/landing/";
var casper = require('casper').create({
    verbose: true,
    logLevel: 'info',
    pageSettings: {
        loadImages: false,      // The WebPage instance used by
                                Casper will
        loadPlugins: false,     // use these settings
        userAgent: 'Mozilla/5.0 (Macintosh; Intel Mac OS X 10_7_5)
AppleWebKit/537.4 (KHTML, like Gecko) Chrome/22.0.1229.94
Safari/537.4'
    }
});
casper.options.viewportSize = {width: 1600, height: 950};
require("utils").dump(casper.cli.args);
require("utils").dump(casper.cli.options);
```

At 1102, Authentication information of the user is retrieved. This is described by the following code in FIG. 11A:

```
// Check for command line arguments and exit if not provided.
if(!(casper.cli.has("user") && casper.cli.has("pass"))){
  console.log("Please provide appropriate command line arugments! Ex. --
user=test@mail.com --pass=qwerty123");
  casper.exit( );
}
var username = String(casper.cli.get("user"));
var password = String(casper.cli.get("pass"));
```

At 1103, the patient's portal login page is opened. This is described by the following code in FIG. 11A:

```
//1. Open up MVMG Patient Portal Login Screen and fillout login
information.
var url = casper.cli.get("url");
if (!url)
    url = "portal.mvmg.com/portal/Login.aspx";
casper.start(url)
```

At 1104, the username and password are set. This is described by the following code in FIG. 11A:

```
.thenEvaluate(function(username,password) {
    document.getElementById("txtUsername").value=username;
    document.getElementById("txtPassword").value=password;
},username,password);
```

At 1105, the submit button is actuated from the navigation menu to log the user in. This is described by the following code in FIG. 11A:

```
//2. Setfocus
casper.then(function( ){
    // Set the focus to allow clicking the login button.
    this.mouse.click(200 , 300);
});
//3. Login!
casper.then(function( ){
    this.evaluate(function( ){
        document.getElementById("btnLogin").click( );
    });
});
```

At 1106 and 1107, the URL paths are navigated if a link is present. This is described by the following code in FIG. 11A:

```
//4. Go to chart-summary page
casper.thenOpen("portal.mvmg.com/portal/chart-summary/default.aspx",
function( ){
});
```

At 1108, if it is determined that more links/URLs exist, control transfers back to 1106, as illustrated. This is described by the following code in FIG. 11A:

```
//5. Render COMPLETE CHART SUMMARY.
casper.then(function( ) {
        this.evaluate(function( ){
document.getElementById("mc_Content_GenericTabs_Gener-
icTabs_lbtnCompleteMedicalRecord").click( );
        });
});
```

If no more URL paths are found, it is presumed the download URL has been received. At 1109, the download button to the health dataset file is actuated. This is described by the following code in FIG. 11A:

```
// 6. Download Complete Chart Summary
// HTTP "GET" REQUEST FOR DOWNLOAD:
// portal.mvmg.com/portal/chart-
summary/handleddownloads/ChartItemDownload/ccddownload/a2f2904b-1f8d-4ece-
b44b-dea96682cf68/Chart-Summary.zip
casper.then(function( ) {
  this.evaluate(function( ){
      document.getElementById("btnDownload").click( );
  });
});
```

At 1110, the downloaded data file is stored for further processing. This is described by the following code in FIG. 11A:

```
casper.on('resource.received', function (resource){
    "use strict";
    if((resource.url.indexOf("/Chart-Summary.zip") !== -1)){
        var url, file;
```

```
        url = resource.url;
        file = "Chart-Summary.zip";
        try {
          var fs = require('fs');
          casper.download(resource.url, destinationPath + file);
        }
        catch(e) {
          this.echo(e);
        }
      }
  });
  casper.run( ); // invoke the above
```

In other embodiments, similar scripts are developed using environments such as Selenium, GreaseMonkey, TamperMonkey, and similar tools which can automate the navigation through a patient portal or other information source, and download information. In FIG. 11, the result is downloading a Continuity of Care document, which is an XML document following HL7 standards. Once the file is downloaded, it is parsed using XPath to extract conditions, problems, procedures, etc. (each to be a type of health information item) and each is then translated into a record, the body map location is calculated as previously described, and the data is stored in the record table (FIG. 7) for later viewing. In one embodiment of the current invention, the health data provider enables access of health data through a REST interface using the FHIR standard, and the configuration information indicates which interfaces to call, supplying parameters as appropriate from configuration data, and accepting the received information into the health information manager 510, thereafter determining the canonical body map location using the previously described method, and storing the combined information in the record table.

FIG. 13 illustrates the operations to perform the tasks to aggregate health records about a patient from various sources and then presenting them in an organized fashion. At 1302, in order to view, and distribute patient health records from multiple sources, a system implementing the techniques described herein, connects to at least one healthcare data provider. At 1304, information related to a user is provided to the at least one healthcare data provider, the information including identification and/or authorization credentials related to the user. In one embodiment, this is achieved by transmitting an attribute associated with a script, where the script is configured to connect to a database or service associated with the healthcare data provider to retrieve the healthcare dataset related to the user. At 1306, a healthcare dataset related to the user is retrieved. In one embodiment, the healthcare dataset includes a set of medical information related to the user. The medical information can include a health condition, procedure, laboratory results, or other data related to the user. In one embodiment, retrieving the healthcare dataset includes navigating through at least one web page configured in a website of the at least one healthcare data provider, and optionally can further include invoking an appropriate link or command to download a health data set from the website. User credentials to log-in to a healthcare provider's systems can be preconfigured by a user and stored in configuration database 550.

At 1308, a corresponding location on a canonical body map related to each medical information in the set of medical information is determined. The list of locations is preconfigured to relate each possible medical information to a corresponding location on the canonical body map. At 1310, the corresponding location and each respective medical information is determined. At 1312, a view of the body map to the user is provided, on a graphical user interface. This may be the canonical body map itself, or an alternate rendition such as an image of the user. In one embodiment, the canonical body map provides markings at each location related to each respective medical information based on the associating. At 1314, medical information is plotted at the location on the body map. If an alternate rendition is used, the location is first converted from the CBM location to the similar location on the alternate rendition. At 1316, display the medical information to the user, with a visual line or pointer to the body location, visually indicating the medical information is related to the marked location on the body map. Further, in one embodiment, an image of the user's body is presented, and the calculated location on the canonical body map is transformed and shown on the image. In another embodiment, the set of medical information displayed at any one time is determined by filters set by the user, enabling viewing of information relative to a particular medical category (such as dermatology, orthopedics, etc), or within a specified time range.

Figure 14:
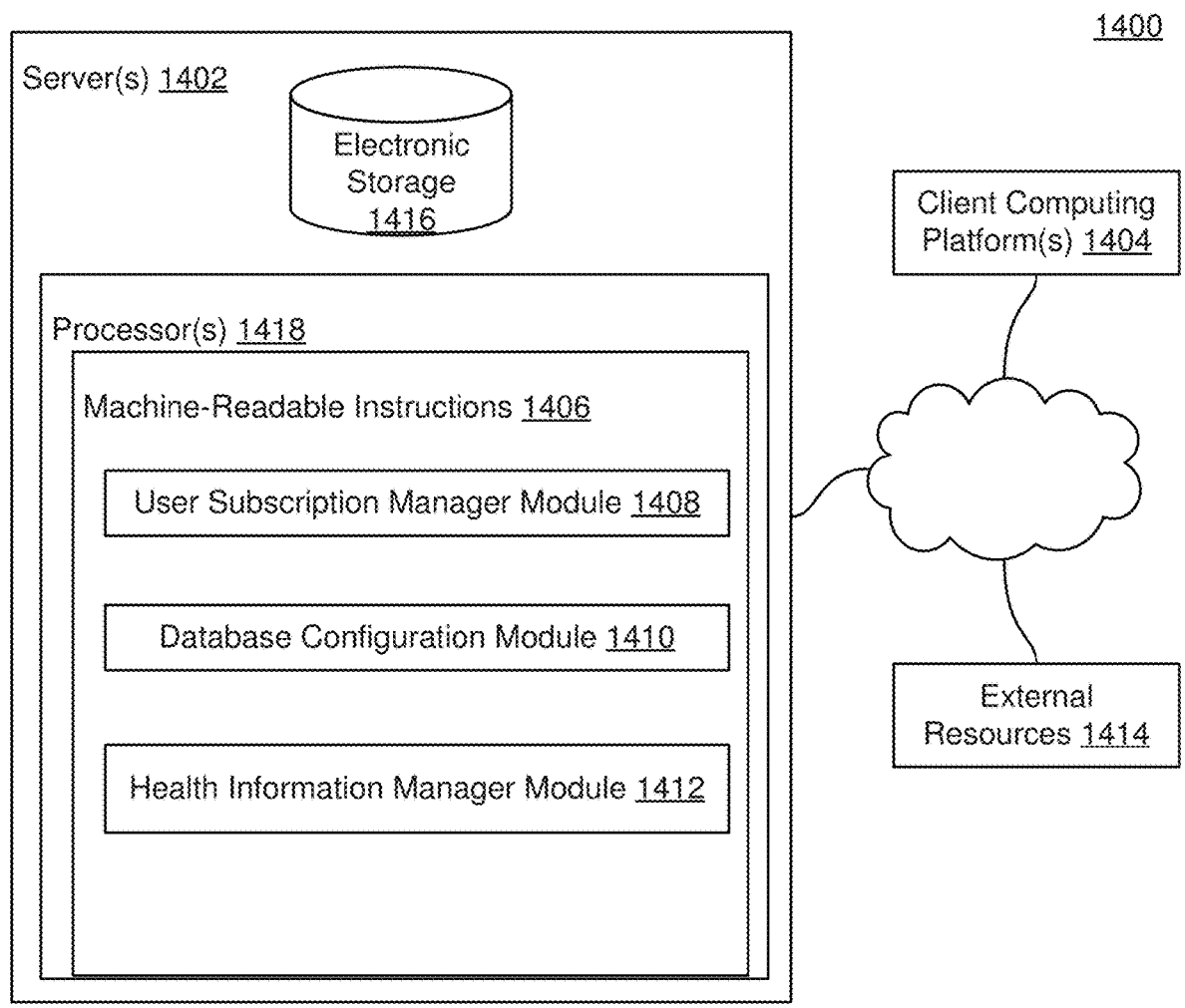
FIG. 14 illustrates a system configured to aggregate and view health records received from multiple sources, according to one aspect of the invention.

FIG. 14 illustrates a system 1400 configured to aggregate and view health records received from multiple sources, in accordance with one embodiment of the invention. In some embodiments, system 1400 can include one or more servers 1402. Server(s) 1402 can be configured to communicate with one or more client computing platforms 1404 according to a client/server architecture and/or other architectures. Client computing platform(s) 1404 can be configured to communicate with other client computing platforms via server(s) 1402 and/or according to a peer-to-peer architecture and/or other architectures. Users can access system 1400 via client computing platform(s) 1404.

Server(s) 1402 can be configured by machine-readable instructions 1406. Machine-readable instructions 1406 can include one or more instruction modules. The instruction modules can include computer program modules. The instruction modules can include one or more of a User Subscription Manager Module 1408, a Database Configuration Module 1410, and a Health Information Manager Module 1412, and/or other instruction modules.

In one embodiment, User Subscription Manager Module 1408 can be configured to subscribe a user to the services for the health information management system 170, as described herein illustrating FIG. 2. Module 1408 can be configured to connect to at least one healthcare data provider. Information related to a user can be provided to the healthcare data provider, the information including identification and/or authorization credentials related to the user. Module 1408 can be configured to retrieve user information from configuration database 550. In one embodiment, this can achieved by transmitting an attribute associated with a script, where the script is configured to connect to a database or service associated with the healthcare data provider, transmit data provided in configuration database 550.

Database Configuration Module 1410 can be configured to provide an interface between module 1408 and system 170, providing instructions to store and retrieve information stored and stored and maintained in the configuration database 550.

Health Information Manager Module 1412 can be configured to retrieve a healthcare dataset related to the user. In one embodiment, the healthcare dataset includes a set of medical information related to the user. The medical information can include a health condition, procedure, laboratory results, or other data related to the user. In one embodiment, retrieving the healthcare dataset includes navigating through at least one web page configured in a website of the at least one healthcare data provider, and optionally can further include invoking an appropriate link or command to download a health data set from the website. Module 1410 can be configured to determine a corresponding location on a canonical body map related to each medical information in the set of medical information is determined. The list of locations can be preconfigured to correspond to each location on the canonical body map. Module 1401 can also be configured to, in one embodiment, to generate a view of the canonical body map to the user via a graphical user interface. In one embodiment, the canonical body map provides markings at each location related to each respective medical information based on the associating. Medical information related to a marking is displayed on the canonical body map through the graphical user interface. Further, in one embodiment, an alternate rendition, such as a photographic image of the user can be displayed, and the location specified in terms of the canonical body map is translated to the corresponding point on the alternative rendition.

In some embodiments, server(s) 1402, client computing platform(s) 1404, and/or external resources 1414 can be operatively linked via one or more electronic communication links. For example, such electronic communication links can be established, at least in part, via a network such as the Internet and/or other networks. It will be appreciated that this is not intended to be limiting, and that the scope of this disclosure includes embodiments in which server(s) 1402, client computing platform(s) 1404, and/or external resources 1414 can be operatively linked via some other communication media.

A given client computing platform 1404 can include one or more processors configured to execute computer program modules. The computer program modules can be configured to enable an expert or user associated with the given client computing platform 1404 to interface with system 1400 and/or external resources 1414, and/or provide other functionality attributed herein to client computing platform(s) 1404. By way of non-limiting example, the given client computing platform 1404 can include one or more of a desktop computer, a laptop computer, a handheld computer, a tablet computing platform, a NetBook, a Smartphone, a gaming console, and/or other computing platforms. External resources 1414 can include sources of information outside of system 1400, external entities participating with system 1400, and/or other resources. In some embodiments, some or all of the functionality attributed herein to external resources 1414 can be provided by resources included in system 1400.

Server(s) 1402 can include electronic storage 1416, one or more processors 1418, and/or other components. Server(s) 1402 can include communication lines, or ports to enable the exchange of information with a network and/or other computing platforms. Illustration of server(s) 1402 in FIG. 14 is not intended to be limiting. Server(s) 1402 can include a plurality of hardware, software, and/or firmware components operating together to provide the functionality attributed herein to server(s) 1402. For example, server(s) 1402 can be implemented by a cloud of computing platforms operating together as server(s) 1402.

Electronic storage 1416 can comprise non-transitory storage media that electronically stores information. The electronic storage media of electronic storage 1416 can include one or both of system storage that is provided integrally (i.e., substantially non-removable) with server(s) 1402 and/or removable storage that is removably connectable to server(s) 1402 via, for example, a port (e.g., a USB port, a firewire port, etc.) or a drive (e.g., a disk drive, etc.). Electronic storage 1416 can include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 1416 can include one or more virtual storage resources (e.g., cloud storage, a virtual private network, and/or other virtual storage resources). Electronic storage 1416 can store software algorithms, information determined by processor(s) 1418, information received from server(s) 1402, information received from client computing platform(s) 1404, and/or other information that enables server(s) 1402 to function as described herein.

Processor(s) 1418 can be configured to provide information processing capabilities in server(s) 1402. As such, processor(s) 1418 can include one or more of a digital processor, an analog processor, a digital circuit designed to process information, an analog circuit designed to process information, a state machine, and/or other mechanisms for electronically processing information. Although processor(s) 1418 is shown in FIG. 14 as a single entity, this is for illustrative purposes only. In some embodiments, processor(s) 1418 can include a plurality of processing units. These processing units can be physically located within the same device, or processor(s) 1418 can represent processing functionality of a plurality of devices operating in coordination. Processor(s) 1418 can be configured to execute modules 1408, 1410, 1412, and/or other modules.

Processor(s) 1418 can be configured to execute modules 1408, 1410, 1412, and/or other modules by software; hardware; firmware; some combination of software, hardware, and/or firmware; and/or other mechanisms for configuring processing capabilities on processor(s) 1418. As used herein, the term "module" can refer to any component or set of components that perform the functionality attributed to the module. This can include one or more physical processors during execution of processor readable instructions, the processor readable instructions, circuitry, hardware, storage media, or any other components.

It should be appreciated that although modules 1408, 1410, and/or 1412 are illustrated in FIG. 14 as being implemented within a single processing unit, in embodiments in which processor(s) 1418 includes multiple processing units, one or more of modules 1408, 1410, and/or 1412 can be implemented remotely from the other modules. The description of the functionality provided by the different modules 1408, 1410, and/or 1412 described below is for illustrative purposes, and is not intended to be limiting, as any of modules 1408, 1410, and/or 1412, can provide more or less functionality than is described. For example, one or more of modules 1408, 1410, and/or 1412 can be eliminated, and some or all of its functionality can be provided by other ones of modules 1408, 1410, and/or 1412. As another example, processor(s) 1418 can be configured to execute one or more additional modules that can perform some or all of the functionality attributed below to one of modules 1408, 1410, and/or 1412.

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

Other features can also be incorporated:

In one embodiment, the information source (for a patient's health data set) is a computer server with an application programming interface (API) allowing similar activities for authentication, information request, and health information retrieval, as described above. The API interface can be implemented in a programming or scripting language which invokes the API in sequence to retrieve the health record information for processing. In one embodiment, an API standard called Fast Healthcare Interoperability Resources ("FHIR") is used by the EHR system to enable a process like the one described above to authenticate and retrieve health information for a patient or user.

In one or more preferred embodiments, the information retrieval process results in downloading a file following a standard called "Consolidated Clinical Document Architecture" ("C-CDA"), which is an XML document following HL7 standards. In one embodiment, health information is retrieved and ingested into the Health Information database on a periodic basis. The system examines each user in the user table. For a given user, the system examines all entries in the fetchJob table, as illustrated in FIG. 6, and for each record performs the following:

(a) Examine the Information Source Table, FIG. 5, corresponding to the fetchJob record, which describes how to gather health information for this user from the indicated health information provider. (b) As specified in the Information Source Table (FIG. 5), establish a connection to the resource on behalf of the user. (c) Follow the defined navigation path, actuating links, buttons and other resources as required and as specified in the designated script or stored navigation path list determined by the Information Source Table, to finally arrive at a link or button that retrieves information from the provider. Invoke this link to download or retrieve the health data.

Thereafter, (d) For each item of information retrieved, perform the following:

(i) Check if the item is already contained in the Health Information Database using a deduplication method where attributes in the retrieved data are compared to attributes in the stored data; (ii) Get the health information from the item, which may include a textual description and/or a code; (iii) Create a record in the "record" table to store the retrieved health information; and (iv) Create a location for a visual text summary of the item, to be shown along with the body map.

In one embodiment, the deduplication method may be extended to take advantage of the hierarchy of terms in the code system used, so that specific terms are known to be related to ancestors in the term hierarchy, and may therefore refer to the same incident, condition, etc. If the record is not new, continue to the next item without storing any information.

Furthermore, if an ICD-9 or ICD-10 code is available, in one embodiment, it can be translated it to a SNOMED-CT code as described herein. In one embodiment, the SNOMED-CT code (whether translated, or provided directly) is examined to find the corresponding "finding site" attribute in the SNOMED-CT data set. The finding site is a reference to a body structure in the SNOMED-CT body structure hierarchy. A reference data set similar to FIG. 12, where the "key" is the SNOMED-CT body structure identifier, is then used to find the location on the canonical body map. The reference data includes a canonical body map location for every SNOMED-CT body structure.

In another embodiment, each word in the item description is used to search the body map keyword reference data for a body map location (see FIG. 12 for example reference data). A word is searched to find the location on the canonical body map. Each word in the problem description in the health record can be searched until a match is found. The coordinate associated with the word is used at the location.

In one embodiment, the visual text summary of the item is shown in a box with color or other visual indication to designate whether the item represents a new condition, ongoing condition, or resolved condition. The location of the text is calculated to be close to the body map location, and not overlapping with the body map other text boxes to the extent possible. A line with similar visual indications is drawn from the text box to the body map location. In order to handle large amounts of information, filters are provided to allow the user to select categories of information (e.g. dermatology, orthopedic, internal, etc). Also, a time filter is included to allow the user to view medical information during a time window (for example over the last 3 years).

In one embodiment, creating a visual rendition is performed as follows:

(a) User selects a particular view which identifies the desired map to render; (b) For each record in the record table with a plot location on the selected map:

(i) Get the point from the record. This is stated in relation to the canonical body map;

(ii) Translate the point onto the custom rendition using the point translation process as described herein; (iii) Place a visual indicator at the translated point on the rendition. This will be on the same approximate location as on the canonical body map (e.g. a point one inch above and to the right of the navel on the canonical body map will appear one inch above and to the right of the navel on the custom rendition); (iv) Place a visual rectangle on the rendition, with textual description as included with the health information (e.g. condition, procedure, treatment, date, etc); and (v) optionally connect the visual rectangle to the location point with a line, thus clearly indicating the information is related to the marked location on the body map.

In one embodiment, data from the user to identify a body point or region, with pertinent data (such as condition, procedure, journal entry, or pain level) is collected. This is implemented by allowing the user to originate a new data entry (condition, procedure, journal entry) affecting a specific location on the body. The user clicks on the body location, and is then prompted for data entry information. The selected body location is translated to the canonical body map prior to further storage and/or processing, and later rendering.

Figure 15:
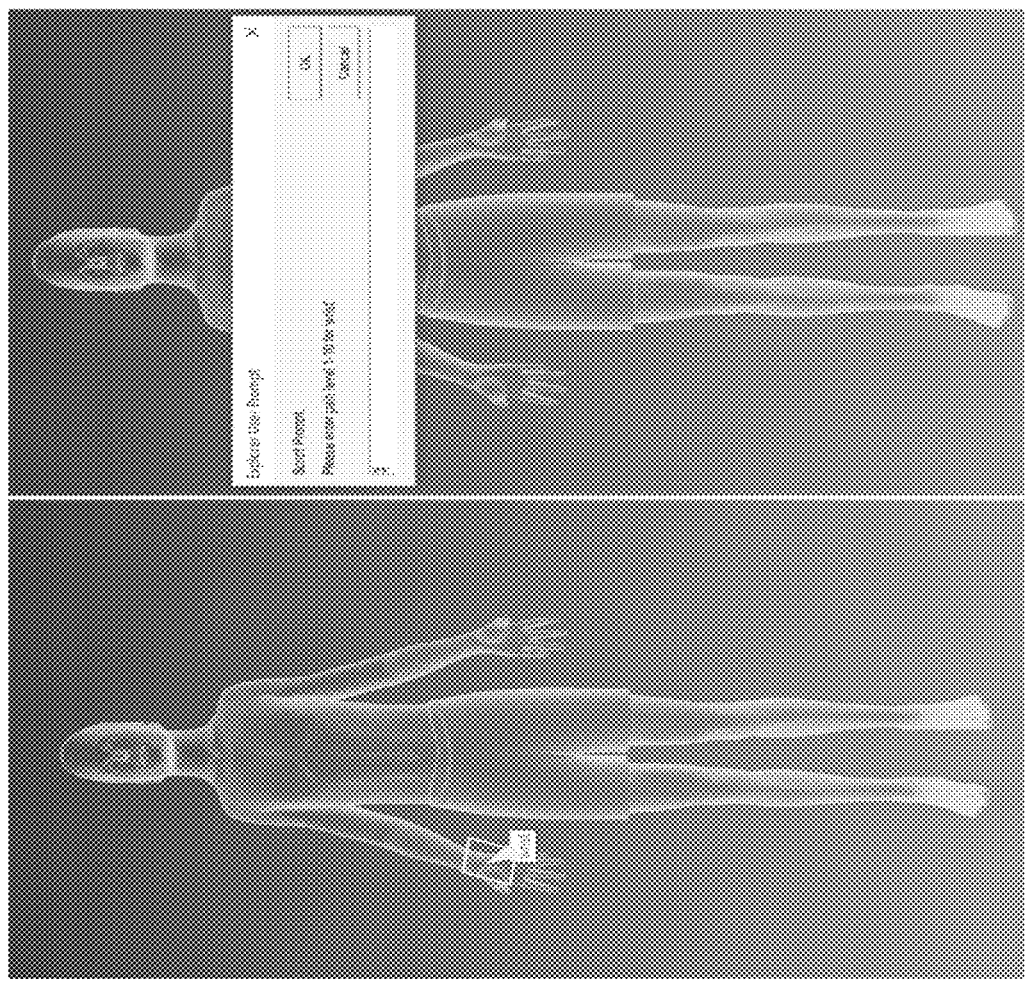
FIG. 15 indicates how one or more polygon regions are defined, allowing the user to select a region and then supply pertinent information such as a pain level, according to one embodiment of the present invention.

In yet another embodiment, pain level information during the management of a disease or recovery from an injury is gathered. The patient can point to a location on the body, and upon prompting, can supply a pain level (for example, a level from a scale of 1 to 10, 10 being the most painful). For example, a Rheumatologist treating a patient may be adjusting prescription types and levels. Pain locations and levels recorded by the patient can inform the Rheumatologist of the success of a treatment plan, and provide guidance for adjustments, if necessary. FIG. 15 indicates how one or more polygon regions are defined, allowing the user to select a region and then supply pertinent information such as a pain level.

The creation of different regions can be accomplished by mapping an element with polygon area definitions that are selectable by the user. Any polygon can be defined as a region.

Figure 16:
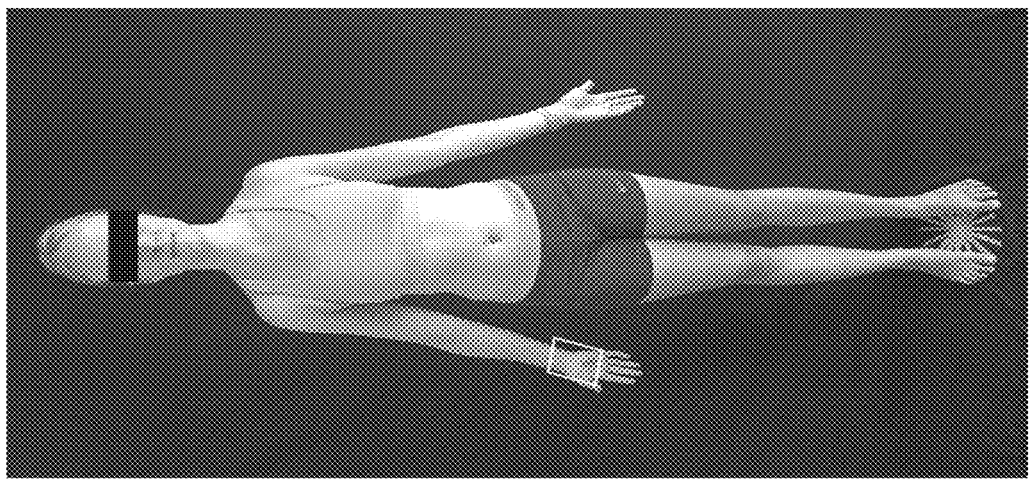
FIG. 16 indicates a translated region, according to one embodiment of the present invention.

The points defining the polygon can then be translated into locations on the canonical body map using the techniques described herein. Thus, in one embodiment, body regions of interest can be defined in a canonical body map, then translated to custom renditions where they can be used for user selection and input. The wrist region in FIG. 15 is thus translated to the wrist region in FIG. 16. The patient is able to view a realistic rendition of themselves during pain level entry, providing better familiarity, which leads to better accuracy in many cases.

In another embodiment, instead of translating the points of a polygon so as to be displayed on a custom rendition, a specific data point can be identified on the custom rendition. This point can be translated to the canonical body map as described herein. Thus, input collected from users with different custom renditions, can be normalized to a common model, in terms of the canonical body map.

Figure 17:
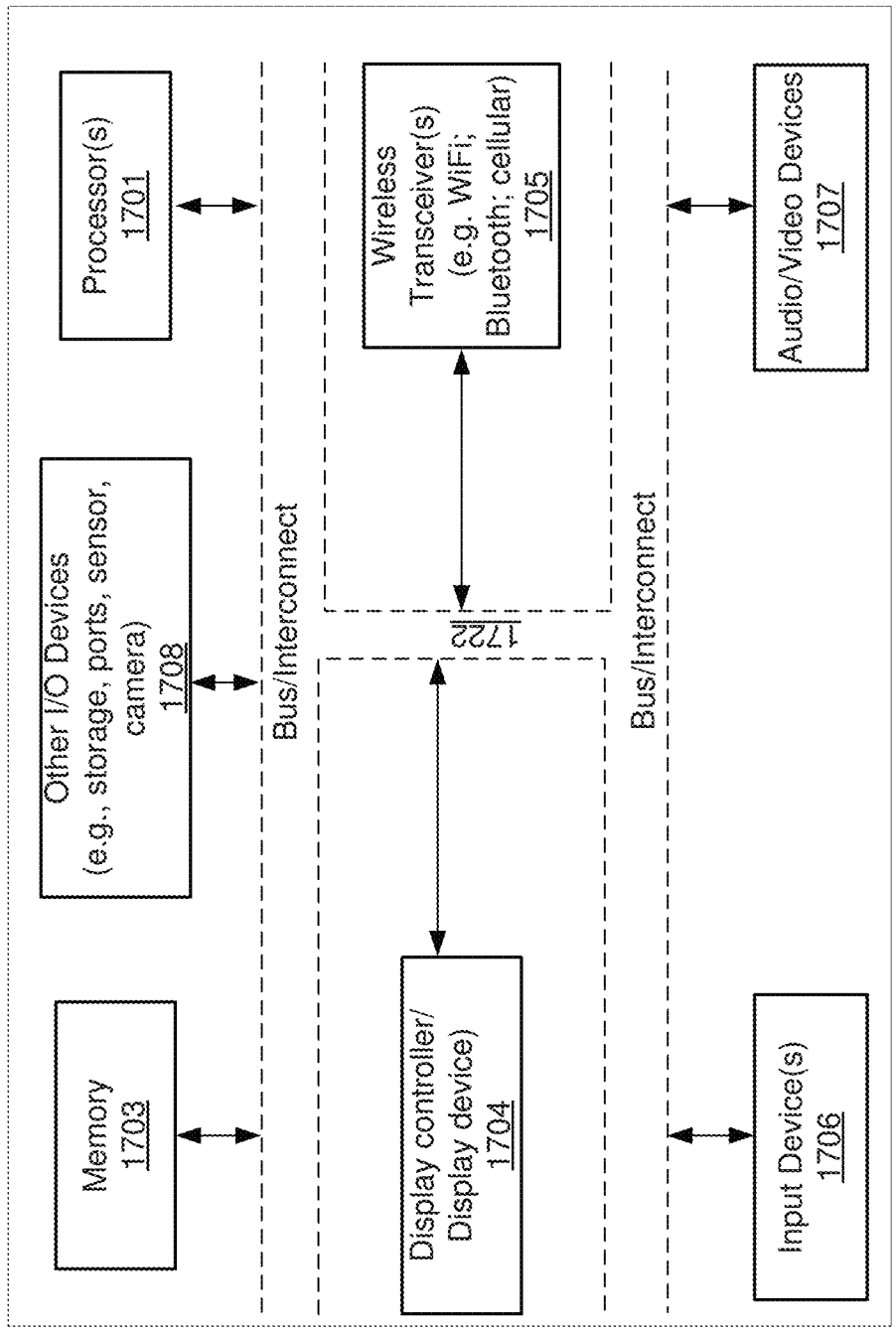
FIG. 17 is a block diagram illustrating a data processing system such as a computing system which may be used with one embodiment of the invention.

FIG. 17 is a block diagram illustrating a data processing system such as a computing system 1700 which may be used with one embodiment of the invention. For example, system 1700 can be implemented for any computing system described herein. It should be apparent from this description that aspects of the present invention can be embodied, at least in part, in software. That is, the techniques may be carried out in a computer system or other computer system in response to its processor, such as a microprocessor, executing sequences of instructions contained in memory, such as a ROM, DRAM, mass storage, or a remote storage device. In various embodiments, hardware circuitry may be used in combination with software instructions to implement the present invention. Thus, the techniques are not limited to any specific combination of hardware circuitry and software nor to any particular source for the instructions executed by the computer system. In addition, throughout this description, various functions and operations are described as being performed by or caused by software code to simplify description. However, those skilled in the art will recognize what is meant by such expressions is that the functions result from execution of the code by a processor.

In one embodiment, system 1700 can represent health information manager 550. System 1700 can have a distributed architecture having a plurality of nodes coupled through a network, or all of its components may be integrated into a single unit. Computing system 1700 can represent any of the data processing systems described above performing any of the processes or methods described above. In one embodiment, computer system 1700 can be implemented as integrated circuits (ICs), discrete electronic devices, modules adapted to a circuit board such as a motherboard, an add-in card of the computer system, and/or as components that can be incorporated within a chassis/case of any computing device. System 1700 is intended to show a high level view of many components of any data processing unit or computer system. However, it is to be understood that additional or fewer components may be present in certain implementations and furthermore, different arrangement of the components shown may occur in other implementations. System 1700 can represent a desktop, a laptop, a tablet, a server, a mobile phone, a programmable logic controller, a personal digital assistant (PDA), a personal communicator, a network router or hub, a wireless access point (AP) or repeater, a set-top box, or a combination thereof.

In one embodiment, system 1700 includes processor 1701, memory 1703, and devices 1705-1708 via a bus or an interconnect 1722. Processor 1701 can represent a single processor or multiple processors with a single processor core or multiple processor cores included therein. Processor 1701 can represent one or more general-purpose processors such as a microprocessor, a central processing unit (CPU), Micro Controller Unit (MCU), etc. Processor 1701 can be a complex instruction set computing (CISC) microprocessor, reduced instruction set computing (RISC) microprocessor, very long instruction word (VLIW) microprocessor, or processor implementing other instruction sets, or processors implementing a combination of instruction sets. Processor 1701 may also be one or more special-purpose processors such as an application specific integrated circuit (ASIC), a cellular or baseband processor, a field programmable gate array (FPGA), a digital signal processor (DSP), a network processor, a graphics processor, a network processor, a communications processor, a cryptographic processor, a co-processor, an embedded processor, or any other type of logic capable of processing instructions. Processor 1701, can also be a low power multi-core processor socket such as an ultra low voltage processor, may act as a main processing unit and central hub for communication with the various components of the system. Such processor can be implemented as a system on chip (SoC).

Processor 1701 is configured to execute instructions for performing the operations and methods discussed herein. System 1700 further includes a graphics interface that communicates with graphics subsystem 1704, which may include a display controller and/or a display device. Processor 1701 can communicate with memory 1703, which in an embodiment can be implemented via multiple memory devices to provide for a given amount of system memory. In various implementations the individual memory devices can be of different package types such as single die package (SDP), dual die package (DDP) or quad die package (QDP). These devices can in some embodiments be directly soldered onto a motherboard to provide a lower profile solution, while in other embodiments the devices can be configured as one or more memory modules that in turn can couple to the motherboard by a given connector. Memory 1703 can be a machine readable non-transitory storage medium such as one or more volatile storage (or memory) devices such as random access memory (RAM), dynamic RAM (DRAM), synchronous DRAM (SDRAM), static RAM (SRAM), or other types of storage devices such as hard drives and flash memory. Memory 1703 may store information including sequences of executable program instructions that are executed by processor 1701, or any other device. System 1700 can further include IO devices such as devices 1705-1708, including wireless transceiver(s) 1705, input device(s) 1706, audio IO device(s) 1707, and other IO devices 1708.

Wireless transceiver 1705 can be a WiFi transceiver, an infrared transceiver, a Bluetooth transceiver, a WiMax transceiver, a wireless cellular telephony transceiver, a satellite transceiver (e.g., a global positioning system (GPS) transceiver), or other radio frequency (RF) transceivers, network interfaces (e.g., Ethernet interfaces) or a combination thereof. Input device(s) 1706 can include a mouse, a touch pad, a touch sensitive screen (which may be integrated with display device 1704), a pointer device such as a stylus, and/or a keyboard (e.g., physical keyboard or a virtual keyboard displayed as part of a touch sensitive screen). Other optional devices 1708 can include a storage device (e.g., a hard drive, a flash memory device), universal serial bus (USB) port(s), parallel port(s), serial port(s), a printer, a network interface, a bus bridge (e.g., a PCI-PCI bridge), sensor(s) (e.g., a motion sensor such as an accelerometer, gyroscope, a magnetometer, a light sensor, compass, a proximity sensor, etc.), or a combination thereof. Optional devices 1708 can further include an imaging processing subsystem (e.g., a camera), which may include an optical sensor, such as a charged coupled device (CCD) or a complementary metal-oxide semiconductor (CMOS) optical sensor, utilized to facilitate camera functions, such as recording photographs and video clips. Certain sensors can be coupled to interconnect 1722 via a sensor hub (not shown), while other devices such as a keyboard or thermal sensor may be controlled by an embedded controller (not shown), dependent upon the specific configuration or design of system 1700.

To provide for persistent storage of information such as data, applications, one or more operating systems and so forth, in one embodiment, a mass storage (not shown) may also couple to processor 1701. In various embodiments, to enable a thinner and lighter system design as well as to improve system responsiveness, this mass storage may be implemented via a solid state device (SSD). However in other embodiments, the mass storage may primarily be implemented using a hard disk drive (HDD) with a smaller amount of SSD storage to act as a SSD cache to enable non-volatile storage of context state and other such information during power down events so that a fast power up can occur on RE-initiation of system activities. Also a flash device may be coupled to processor 1701, e.g., via a serial peripheral interface (SPI). This flash device may provide for non-volatile storage of system software, including a basic input/output software (BIOS) as well as other firmware of the system.

Note that while system 1700 is illustrated with various components of a data processing system, it is not intended to represent any particular architecture or manner of interconnecting the components; as such details are not germane to embodiments of the present invention. It will also be appreciated that network computers, handheld computers, mobile phones, and other data processing systems which have fewer components or perhaps more components may also be used with embodiments of the invention.

While the above detailed description has shown, described, and pointed out the fundamental novel features of the disclosure as applied to various implementations, it will be understood that various omissions and substitutions and changes in the form and details of the system illustrated may be made by those skilled in the art, without departing from the intent of the disclosure. Although the present invention has been described with reference to specific exemplary embodiments, it will be evident that various modifications and changes may be made to these embodiments without departing from the broader spirit and scope of the invention as set forth in the claims. Accordingly, the specification and drawings are to be regarded in an illustrative rather than a restrictive sense.

What is claimed is:

1. A method, comprising:
   instantiating, by a computer system, a web browser object in memory, wherein the web browser object includes information related to a user;
   connecting, by the computer system, using the web browser object in memory, to a server of at least one healthcare data provider;
   providing, by the computer system, using the web browser object in memory, the information related to a user to the at least one healthcare data provider;
   receiving, by the computer system, using the web browser object in memory, Extensible Markup Language (XML) based retrieving a healthcare dataset related to the user;
   parsing, by the computer system, the XML based healthcare dataset using XML Path Language (XPath) to query XML nodes of the healthcare dataset to extract at least one health data item related to the user;
   determining, by the computer system, a corresponding location on a canonical body map related to the at least one health data item;
   associating, by the computer system, the corresponding location with the at least one health data item;
   providing, by the computer system, a view of the canonical body map to the user wherein the canonical body map provides a marking associating the at least one health data item; and
   displaying, by the computer system, information related to the at least one health data item, when the user interacts with the canonical body map through a graphical user interface coupled to the computer system.

2. The method of claim 1, wherein the canonical body map can be replaced with an alternate rendition, the alternate rendition including an image of a body of the user.

3. The method of claim 1, wherein providing the information related of the user to the at least one healthcare data provider includes transmitting an attribute associated with a script, wherein the script is configured to connect to a database associated with the healthcare data provider to retrieve the healthcare dataset related to the user.

4. The method of claim 1, wherein the corresponding location on the canonical body map associated with the at least one health data item is preconfigured.

5. The method of claim 1, wherein retrieving the healthcare dataset includes navigating through at least one web page configured in a website of the at least one healthcare data provider.

6. The method of claim 5, wherein retrieving the healthcare dataset includes invoking an appropriate link or command to download a health data set from the website.

7. The method of claim 1, wherein the at least one health data item includes data related to a health condition, procedure, or laboratory results related to the user.

8. A non-transitory computer readable medium comprising instructions which when executed by a processing system performs a method, comprising:
   instantiating a web browser object in memory, wherein the web browser object includes information related to a user;
   connecting, using the web browser object in memory, to a server of at least one healthcare data provider;
   providing, using the web browser object in memory, the information related to a user to the at least one healthcare data provider;
   receiving Extensible Markup Language (XML) based a healthcare dataset related to the user;
   parsing the XML based healthcare dataset using XML Path Language (XPath) to query XML nodes of the healthcare dataset to extract at least one health data item related to the user;
   determining a corresponding location on a canonical body map related to the at least one health data item;
   associating the corresponding location with the at least one health data item;

providing a view of the canonical body map to the user, on a graphical user interface, wherein the canonical body map provides a marking associating the at least one health data item; and displaying information related to the at least one health data item, when the user interacts with the canonical body map through a graphical user interface.

9. The non-transitory computer readable medium of claim 8 wherein the canonical body map can be replaced with an alternate rendition, the alternate rendition including an image of a body of the user.

10. The non-transitory computer readable medium of claim 8, wherein providing the information related of the user to the at least one healthcare data provider includes transmitting an attribute associated with a script, wherein the script is configured to connect to a database associated with the healthcare data provider to retrieve the healthcare dataset related to the user.

11. The non-transitory computer readable medium of claim 8, wherein the corresponding location on the canonical body map associated with the at least one health data item is preconfigured.

12. The non-transitory computer readable medium of claim 8, wherein retrieving the healthcare dataset includes navigating through at least one web page configured in a website of the at least one healthcare data provider.

13. The non-transitory computer readable medium of claim 8, wherein retrieving the healthcare dataset includes invoking an appropriate link or command to download a health data set from the website.

14. The non-transitory computer readable medium of claim 8, wherein the at least one health data item includes data related to a health condition, procedure, or laboratory results related to the user.

15. A system comprising:
a memory module;
a processing system comprising at least one hardware core coupled to the memory module configured to:
instantiate a web browser object in the memory module, wherein the web browser object includes information related to a user;
connect, using the web browser object in the memory module, to a server of at least one healthcare data provider;

provide, using the web browser object in the memory module, the information related to a user to the at least one healthcare data provider;

receive, using the web browser object in the memory module, Extensible Markup Language (XML) based retrieving a healthcare dataset related to the user;

parse the XML based healthcare dataset using XML Path Language (XPath) to query XML nodes of the healthcare dataset to extract at least one health data item related to the user;

determine a corresponding location on a canonical body map related to the at least one health data item;

associate the corresponding location with the at least one health data item;

provide a view of the canonical body map to the user, wherein the canonical body map provides a marking associating the at least one health data item; and display information related to the at least one health data item, when the user interacts with the canonical body map through a graphical user interface.

16. The system of claim 15, wherein the canonical body map can be replaced with an alternate rendition, the alternate rendition including an image of a body of the user.

17. The system of claim 15, wherein to provide the information related of the user to the at least one healthcare data provider includes transmitting an attribute associated with a script, wherein the script is configured to connect to a database associated with the healthcare data provider to retrieve the healthcare dataset related to the user.

18. The system of claim 15, wherein the corresponding location on the canonical body map associated with the at least one health data item is preconfigured.

19. The system of claim 15, wherein to retrieve the healthcare dataset includes navigating through at least one web page configured in a website of the at least one healthcare data provider.

20. The system of claim 15, wherein to retrieve the healthcare dataset includes invoking an appropriate link or command to download a health data set from the website, and wherein the at least one health data item includes data related to a health condition, procedure, or laboratory results related to the user.

* * * * *